(12) United States Patent
Wang et al.

(10) Patent No.: US 8,460,285 B2
(45) Date of Patent: Jun. 11, 2013

(54) ABLATION CATHETER ELECTRODE HAVING MULTIPLE THERMAL SENSORS AND METHOD OF USE

(75) Inventors: Huisun Wang, Maple Grove, MN (US); Hong Cao, Savage, MN (US); Jeremy D. Dando, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1664 days.

(21) Appl. No.: 11/647,282

(22) Filed: Dec. 29, 2006

(65) Prior Publication Data
US 2008/0161797 A1  Jul. 3, 2008

(51) Int. Cl.
*A61B 18/18* (2006.01)

(52) U.S. Cl.
USPC ............................................. 606/41; 606/45

(58) Field of Classification Search
USPC .................................................. 606/40–46
See application file for complete search history.

(56) References Cited

U.S. PATENT DOCUMENTS

| | | |
|---|---|---|
| 3,513,432 A | 5/1970 | Davis |
| 3,595,079 A | 7/1971 | Grahn |
| 3,817,109 A | 6/1974 | Audet et al. |
| 3,951,136 A | 4/1976 | Wall |
| 4,075,036 A | 2/1978 | Lysikov et al. |
| 4,240,441 A | 12/1980 | Khalil |
| 4,654,024 A | 3/1987 | Crittenden et al. |
| 5,138,363 A | 8/1992 | Yuge |
| 5,199,789 A | 4/1993 | Mauric |
| 5,228,442 A | 7/1993 | Imran |
| 5,231,995 A | 8/1993 | Desai |
| 5,263,493 A | 11/1993 | Avitall |
| 5,281,217 A | 1/1994 | Edwards et al. |
| 5,433,708 A | 7/1995 | Nichols et al. |
| 5,435,308 A | 7/1995 | Gallup et al. |
| 5,542,928 A | 8/1996 | Evans et al. |
| 5,582,609 A | 12/1996 | Swanson et al. |
| 5,611,338 A | 3/1997 | Gallup et al. |
| 5,688,267 A | 11/1997 | Panescu et al. |
| 5,697,925 A | 12/1997 | Taylor |
| 5,735,605 A | 4/1998 | Blalock |
| 5,810,802 A | 9/1998 | Panescu et al. |
| 5,833,688 A | 11/1998 | Sieben et al. |
| 5,874,899 A | 2/1999 | Barmore, Jr. et al. |
| 5,897,552 A * | 4/1999 | Edwards et al. ............ 606/31 |
| 6,015,407 A * | 1/2000 | Rieb et al. ............... 606/41 |
| 6,099,524 A | 8/2000 | Lipson et al. |
| 6,113,591 A * | 9/2000 | Whayne et al. ............ 606/34 |
| 6,293,943 B1 | 9/2001 | Panescu et al. |

(Continued)

OTHER PUBLICATIONS

International Search Report for PCT/US2007/088638 dated May 16, 2008 and Written Opinion of Searching Authority.

*Primary Examiner* — Linda Dvorak
*Assistant Examiner* — Amanda Scott
(74) *Attorney, Agent, or Firm* — Wiley Rein LLP

(57) ABSTRACT

The invention relates to electrodes used in ablation catheter devices, where the electrodes contain two or more thermal sensors at different positions within the electrode that are capable of detecting temperature differences along the external surface of the electrode. In preferred embodiments, the thermal sensors are separated by one or more thermal insulating members and the thermal sensors are positioned near the external surface of the electrode at about the same distance from the end of the electrode, so that temperature measurements can indicate the position of the electrode with respect to the tissue desired to be ablated.

15 Claims, 6 Drawing Sheets

U.S. PATENT DOCUMENTS

| | | |
|---|---|---|
| 6,312,425 B1 * | 11/2001 | Simpson et al. ............... 606/32 |
| 6,322,558 B1 | 11/2001 | Taylor et al. |
| 6,451,011 B2 | 9/2002 | Tu |
| 6,471,693 B1 | 10/2002 | Carroll et al. |
| 6,616,657 B2 | 9/2003 | Simpson et al. |
| 6,730,077 B2 | 5/2004 | Carroll et al. |
| 6,942,661 B2 | 9/2005 | Swanson |
| 6,979,329 B2 | 12/2005 | Burnside et al. |
| 7,326,204 B2 | 2/2008 | Paul et al. |
| 2005/0159739 A1 | 7/2005 | Paul et al. |

* cited by examiner

ABLATION CATHETER ELECTRODE HAVING MULTIPLE THERMAL SENSORS AND METHOD OF USE

BACKGROUND OF THE INVENTION a. Field of the Invention

The instant invention relates generally to devices and methods for ablating tissue. The diagnosis and treatment of electrophysiological diseases of the heart are described in connection with the devices and methods of the present invention. In particular, the instant invention relates to devices and methods related to cardiac ablation for the treatment of atrial fibrillation, as well as the advantages of devices that employ more accurate temperature monitoring during ablation at selected cardiac sites.

b. Background Art

It is well known that atrial fibrillation results from disorganized electrical activity in the heart muscle, or myocardium. The surgical "Maze" procedure has been developed for treating atrial fibrillation and involves the creation of a series of surgical incisions through the atrial myocardium in a preselected pattern to create conductive corridors of viable tissue bounded by non-conductive scar tissue.

In performing the Maze procedure and its variants, whether using ablation or surgical incisions, it is generally considered most efficacious to include a transmural incision or lesion that isolates the pulmonary veins from the surrounding myocardium. The pulmonary veins connect the lungs to the left atrium of the heart. The Maze procedures have been found to offer 57-70% success without antiarrhythmic drugs. However, they are also associated with a 20-60% recurrence rate several possible factors, including incomplete lesions, lesion recovery, non-pulmonary vein foci of the arrhythmia, or the need for further tissue modifications.

As an alternative to the surgical incisions used in the Maze procedure, transmural ablations of the heart have also been used. The use of catheters for ablating specific locations within the heart has been disclosed, for example in U.S. Pat. Nos. 4,641,649, 5,263,493, 5,231,995, 5,228,442 and 5,281,217. Such ablations may be performed either from within the chambers of the heart (endocardial ablation) using endovascular devices (e.g., catheters) introduced through arteries or veins, or from outside of the heart (epicardial ablation) using devices introduced into the chest. Various ablation techniques have been used, including cryogenic, radiofrequency (RF), laser and microwave ablation. The ablation devices are used to create transmural lesions—that is, lesions extending throughout a sufficient thickness of the myocardium to block electrical conduction, which effectively forms boundaries around the conductive corridors in the atrial myocardium. Perhaps the most advantageous aspect of the use of transmural ablation rather than surgical incisions is the ability to perform the procedure on the beating heart without the use of cardiopulmonary bypass.

Producing precise transmural lesions during cardiac ablation presents significant obstacles for the physician for several reasons. First, the elongated and flexible vascular ablation devices are difficult to manipulate into the complicated geometries required for forming the lesions. Additionally, maintaining the proper positioning against the wall of a beating heart can be difficult. Also, visualization of cardiac anatomy and vascular devices is often inadequate which makes identifying the precise position of such devices in the heart difficult, which can result in misplaced lesions.

During an ablation procedure, precise temperature regulation of the tissue under ablation is another issue encountered by the physician. Tissue ablation generally begins to occur at 50° C., while over-heating occurs at around 100° C. It can be important to monitor the temperature of the tissue during ablation. Most ablation devices accomplish this by measuring the electrode temperature during the ablation. The most common way to monitor the electrode temperature is to install a thermal sensor (e.g., thermocouple or thermistor) inside the tip electrode to measure its temperature.

One of the shortcomings of current methods of monitoring electrode temperature is that the cylindrical shape of a typical ablation catheter tip often means that only a portion of the catheter tip is in direct contact with the ablation surface. Generally, the catheter electrodes themselves do not retain a great deal of thermal energy because they are made of materials with extremely high thermal conductivity, for instance, metals. Thus, the highest temperatures on the electrode itself are generally seen on that portion of the electrode which is direct contact with the tissue surface. Conversely, portions of the electrode not in direct contact with target tissue are most likely contacting blood or interstitial fluids. Since these fluids can conduct a significant amount of heat away from the ablating tissue, temperatures measured in the blood or interstitial fluid may appear to be significantly cooler than the ablating tissue temperature.

Temperature monitoring devices that rely on measuring a point temperature on an electrode with only a single sensor can skew tissue temperature readings by other mechanisms. Since an ablation electrode tip can be quite long in comparison with the diameter of a catheter, the contact angle between the catheter and the ablating tissue can also be a significant factor. For instance, consider the case of a catheter electrode that is positioned with only its distal end contacting on the tissue. If the temperature sensor is located on the proximal end of the electrode (which is not in contact with the tissue) then a significantly different temperature reading from the one present at the tissue may be measured. Whether the result of tissue-contacting angle or conduction of heat away from the electrode, the monitoring of only a single point temperature can produce misleading readings of the temperature at an ablation surface.

If presented with an inaccurate temperature reading, a physician may apply an inappropriate amount of ablation energy to the site. If a tissue being ablated does not reach a sufficiently high temperature for a sufficient period of time, the target tissue may receive an incomplete ablation, which can significantly affect the efficacy of the treatment. On the other hand, excessively high electrode temperatures can cause tissue steam-pop, tissue-charring, or other serious over-heat related tissue damage. Additionally, blood contacting an overheated electrode can lead to the formation of coagulum, which can present thrombo-embolitic hazards to the patient.

The limitations of single point temperature monitoring are well known and several attempts have been made to overcome their disadvantages. U.S. Pat. No. 6,312,425 (Simpson, et. al.) discusses a design using multiple thermal sensors to monitor the temperature in a tip electrode. Simpson describes an arrangement of thermal sensors where one sensor is positioned at the distal apex of the tip and a plurality of other thermal sensors are positioned around the circumference of the electrode in a more proximal location on the catheter. Since the highest temperatures are most likely to be found at the portion of the electrode making contact with target tissue, by monitoring and comparing the temperature reading at the distal end of the electrode to that at the proximal end, a determination can be made of both the maximum temperature being experienced by the tissue and which end of the electrode is performing the ablation.

Similarly, U.S. Pat. No. 6,616,657 (by the same inventors) discusses a method of using the multiple temperature sensors to determine the orientation of the catheter. Experience with that device has shown that the variation in temperature between the end in contact with tissue and the non-contacting end is approximately 10° C. Therefore, an ablation which is showing a temperature at the distal apex of the electrode that is 10° warmer than the proximal sensor is assumed to be in an "end-firing" position—with the distal end of the catheter providing all of the ablation energy to the tissue. Similarly, an observation that the proximal ports are 10° warmer than the distal sensor means that the electrode is in a "side-firing" position—with only the side portion of the catheter contacting the tissue. Temperature differences falling somewhere between 1-10° are assumed to indicate a contacting angle between these two extremes.

The thermal sensors described in each of the above publications are positioned at different ends of a relatively long electrode. However, it is often desirable to use a short electrode during an ablation procedure in order to improve RF energy transfer efficiency. A typical short electrode of this type has an electrode length of approximately 2.0-2.5 mm. This length is roughly comparable to the diameter of most ablation catheters. As mentioned previously, most ablation electrodes are made from materials having excellent thermal conductivity. In these situations, placement of temperature sensors at the proximal and distal ends of a relatively short electrode may create an undesirable situation where the temperature differences between the sensors will not be significant enough to measure because of the rapid conduction of heat energy from one end of the electrode to the other.

What are needed, therefore, are devices and methods which allow for precise temperature measurement at several points in relatively short ablation electrodes. The devices and methods would preferably allow the physician to accurately measure the maximum temperature experienced by a target tissue during a thermal ablation and provide information that would allow the physician to determine the extent and orientation of contact between the ablating electrode and the target tissue.

BRIEF SUMMARY OF THE INVENTION

It is desirable to be able to detect and determine the maximum temperature experienced by a target tissue during an ablation procedure. Accurate determination of maximum temperature of an electrode at the target tissue provides increased safety to the patient and can provide the physician with information useful in the placement of ablation catheters, such as the orientation of the ablating surfaces.

The present invention meets these and other objectives by providing devices and methods for accurately measuring the temperature of an ablation electrode when in contact with tissue, and monitoring temperature changes during an ablation procedure. In one aspect, the invention integrates an ablation catheter having an electrode assembly with at least two thermal sensors disposed near the external surface of the electrode ablating surfaces. The thermal sensors are separated by a thermal insulation member, which functions to thermally shield one thermal sensor from another to effectively produce two or more temperature measurements from two or more different points along the surface of the electrode. The results of the positioning of the thermal sensors combined with the separate temperature measurements at those positions can lead to a determination of the orientation of the ablating electrode and its external surfaces with respect to a target tissue. The invention is especially advantageous when a smaller ablating electrode is used, where the electrode length is approximately the same as its outer diameter in the case of a cylindrical electrode, or approximately the same as the cross-sectional length when other shapes are employed. With the preferred size of electrodes of about 2.5 mm or about 2.0 mm in diameter and length, the thermal sensors cannot be effectively positioned at distal (or near the terminal end) and proximal (near the elongated catheter body end) areas of the electrode to generate temperature measurements at different ends of the electrode. By employing the electrodes described here, one of skill in the art can position thermal sensors at approximately the same distance from a distal end of the electrode and at different positions along the circumferential or external surface of cylindrical electrodes, for example. The measurement of temperatures from thermal sensors positioned in this manner can advantageously be used to determine which side or surface of the electrode is in contact with tissue and which is not. Furthermore, the use of thermal insulating members or materials to shield one thermal sensor from another, or create distinct isothermal zones of the electrode, provides more accurate temperature measurements.

In preferred embodiments, the device of the invention comprises an electrode for an ablation catheter, where the tip has a distal end or tip, a partially hollowed core or body region, and a proximal region that is connected to the catheter with elongated end with control functions and a power source for activating an ablation procedure. The tip electrode is designed to incorporate at least two thermal sensors within the partially hollowed core or body region and preferably near the external surface of the electrode. The positioning of the thermal sensors with respect to thermal insulating material or members can effectively shield one thermal sensor from the temperature changes that might occur at the electrode surface near another thermal sensor. Thus, for example, one region of the electrode tip in contact with tissue may register a higher temperature than a region that is not in contact with tissue, and in small electrodes the proximity of these regions can cause both of the thermal sensors to register higher temperatures. Shielding a thermal sensor will substantially reduce the transfer of heat in a metallic electrode. Accordingly, more accurate temperature measurements from each positioned thermal sensor can be rendered into precise orientation information on the electrode tip and its placement on tissue or in the body.

In another aspect, the invention comprises a method of manufacturing an electrode as described. Employing the partially hollowed region or cuts or slots from a side of the electrode, the manufacture or production of an electrode with multiple isothermal zones, each having a thermal sensor and separated by an insulation member or element, is relatively simple compared to other electrodes having thermal sensors at distal and proximal regions. For example, laser cutting or simple drilling of the metallic electrode from one end can be used to prepare holes or slots to accommodate a thermal sensor in appropriate positions and to accommodate the thermal insulation member or element. As describe here, the positioning of the thermal sensors and insulating members can vary. In preferred aspects where a 2.5 mm electrode is used, the thermal sensors can be positioned at about 0.25 mm from the external surface of the electrode through the use of the laser cutting or drilling process. Filling the hollow or partially hollowed region or holes or slots in the electrode with an appropriate polymer or adhesive can affix the thermal sensors and insulating members in place, and the polymer or adhesive selected can also provide some insulating properties to the electrode design. However, the shape, placement and material selected for the insulating members or elements are preferably employed in a manner where the insulating member is a separate and defined shape from the adhesive or affixing compound, as shown in some of the examples of the figures. Thus, in particular embodiments the methods of the invention encompass using a cylindrical or shaped metal or metal alloy electrode having a length approximately equal to its diameter, cutting three or more slots or holes in the base of the electrode opposite a distal end or tip to create a partially hollowed core region, filling or inserting a thermal insulation member into a slot or hole, and inserting two or more thermal sensors into different slots or holes such that the thermal insulation member separates at least two thermal sensors, effectively creating an isothermal zone for each thermal sensor.

In an advantageous aspect of the invention, the ablation catheter electrode is used to determine the orientation of the ablating surface by measuring the temperature at the thermal sensors or measuring the changes in temperature over time. These measurements can be used to determine the orientation of the electrode in contact with a target tissue.

The foregoing and other aspects, features, details, utilities, and advantages of the present invention will be apparent from reading the following description and claims, and from reviewing the accompanying drawings.

DETAILED DESCRIPTION OF THE INVENTION

The headings (such as "Brief Summary") used are intended only for general organization of topics within this disclosure and are not intended to limit the disclosure of the invention or any aspect of it. In particular, subject matter disclosed in the "Background Art" may include aspects of technology within the scope of the invention and thus may not constitute solely background. Subject matter disclosed in the "Brief Summary" is not an exhaustive or complete disclosure of the entire scope of the invention or any particular embodiment.

As used herein, the words "preferred," "preferentially," and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention and no disclaimer of other embodiments should be inferred from the discussion of a preferred embodiment or a figure showing a preferred embodiment.

Figure 1:
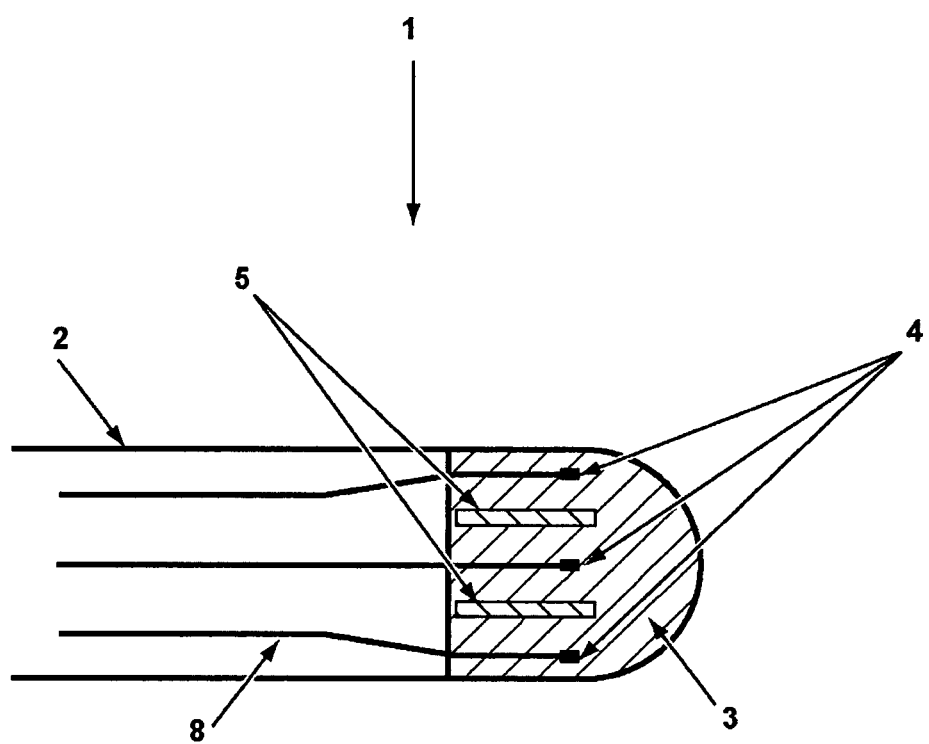
FIG. 1 is a diagram of an embodiment of an ablation catheter including a tip electrode, thermal sensors located at approximately the same distance from the electrode tip, and insulation members separating the thermal sensors.

In one aspect of the invention, FIG. 1 depicts an ablation catheter assembly (1) comprising an elongated shaft catheter body (2) having a proximal end and distal end connected to an ablation tip electrode (3), a plurality of thermal sensors (4) arranged around the circumference of the electrode, at the same distance from the distal end dome-shaped region, and near the external surface of the electrode, and at least one insulation member or member (5) within the electrode that functions to thermally isolate the temperature sensors from one another. The tip electrode can be made from any appropriate electrically and thermally conductive biocompatible material. Appropriate electrode materials can include silver, gold, chromium, aluminum, molybdenum, tungsten, nickel, and platinum (Pt). Preferred embodiments contain an electrode made from Pt, or a Pt/iridium (Ir) alloy, such as alloys with about 1 to about 10% Ir.

Figure 2:
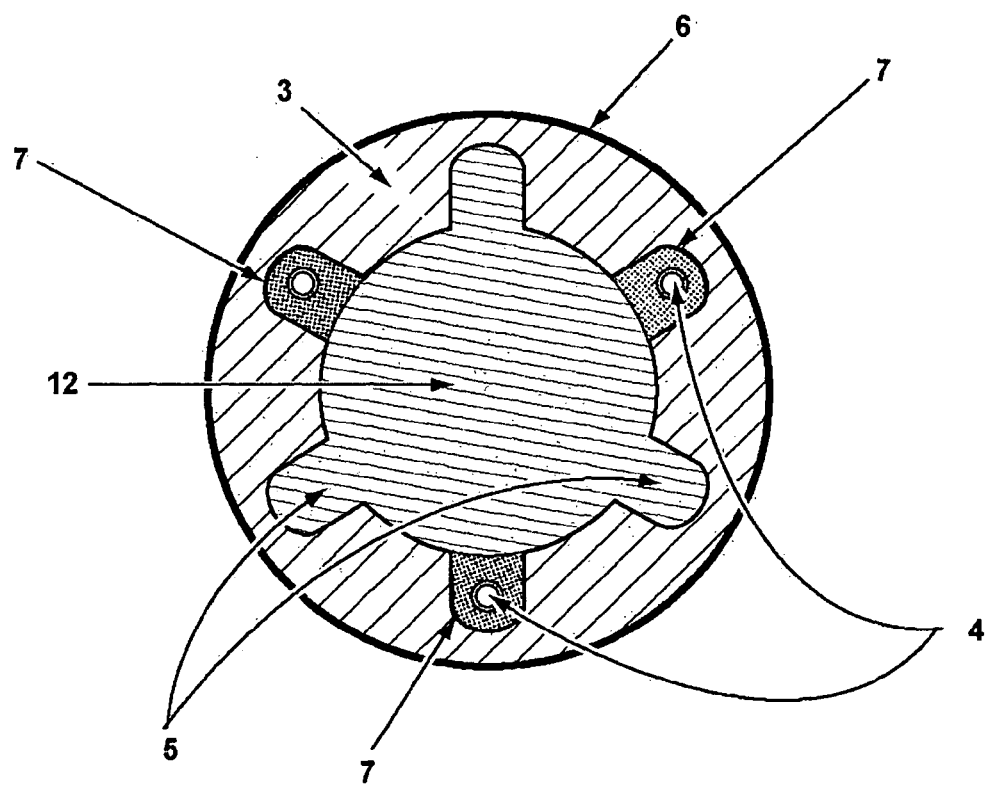
FIG. 2 is a cross-section view of the electrode assembly showing one arrangement of symmetrically spaced and alternating thermal sensors and insulation members.

FIGS. 1 and 2 show an arrangement of three thermal sensors located in the electrode. Preferred embodiments include 3 or 4 sensors located around the circumference of the electrode although lesser and greater numbers of sensors are also contemplated by this disclosure. The use of thermal sensors in ablation electrodes is well known and the sensors themselves are usually of a thermocouple or thermistor-type design. FIG. 1 also shows the attachment of electrical leads (8) to the thermal sensors in the electrode, which can be fed back through the shaft of the catheter to monitoring or control equipment on the proximal end. A separate power lead (not shown) conducts power to the tip electrode (3) during the ablation of target tissue.

Figure 3:
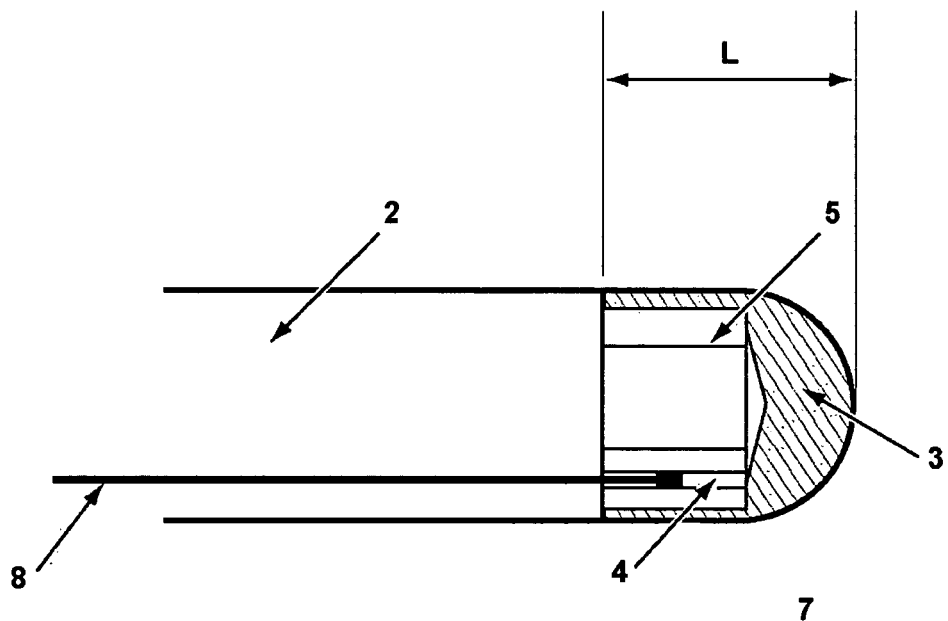
FIG. 3 is different cross-sectional view of the electrode that also shows one of the thermal sensors (top) and one of the insulation members (bottom) in an electrode with approximately the same length (L) as diameter.

FIG. 2 shows a radial cross-sectional view of the tip electrode with an arrangement of three sensors (4). As shown, the sensors may be arranged in a symmetrical manner around the circumference of the electrode and near the external surface of the electrode. Other numbers of temperature or thermal sensors may also be arranged in a symmetrical pattern. However, certain applications may make it more desirable to arrange the sensors in an asymmetric pattern around the electrode, and embodiments using asymmetric arrangements of sensors are specifically contemplated in this application. FIG. 3 also schematically depicts the symmetrical arrangement of thermal insulating members (5) within slots extending radially from the center of the tip electrode (3). A central hollowed region shown in this embodiment can house the leads and can be filled with an appropriate adhesive or polymer to fix the positions of the thermal sensors (4) and insulating members (5). In the arrangement of FIG. 2, each thermal sensor is effectively thermally isolated, so that the temperature difference that may exist during an ablation procedure from one side or region of the electrode surface can be detected.

FIG. 3 is a longitudinal cross-section view of the ablation electrode (3) at the distal end of catheter (1). In a preferred embodiment, FIG. 3 describes what is known in the art as 2½ mm (length) ablation assembly, represented by the distance (L). A 2½ mm ablation assembly is often preferred because it requires less power (around 10-20 W, as compared to around 20-40 W for a 4 mm assembly). However, it is contemplated that any size and shape ablation electrode, including a 4 mm tip assembly or ring electrode assemblies, are equally possible for use in the current invention. For example, in instances where a larger ablation area is desired to provide a different orientation of the electrode assembly, for example in FIG. 6, a larger surface electrode area can be accommodated, while still yielding the desirable separation between the thermal sensors (4).

In preferred embodiments, it is desirable for the thermal sensors (4) to be installed at a depth of approximately 0.01 mm from the outer or external surface of the electrode of the invention. The position of the installed thermal sensor may be described in reference to a virtual circumferential line drawn around the external surface of the electrode at a constant distance from an electrode end or tip. Circumferential lines with radii less than the outer surface circumference line can be used for describing the precise depth of the thermal sensor below the external surface of the electrode. The thermal sensors may be secured into position within the electrode by use of an epoxy adhesive, or any other biocompatible adhesive, filled into a bored hole or slot (7) in the electrode of FIGS. 2 and 3. The areas of the holes or slots may be filled with the adhesives or polymers as noted above to affix the thermal sensors and thermal insulating member as well as fill the interior of any hollowed core region (12).

Figure 4A:
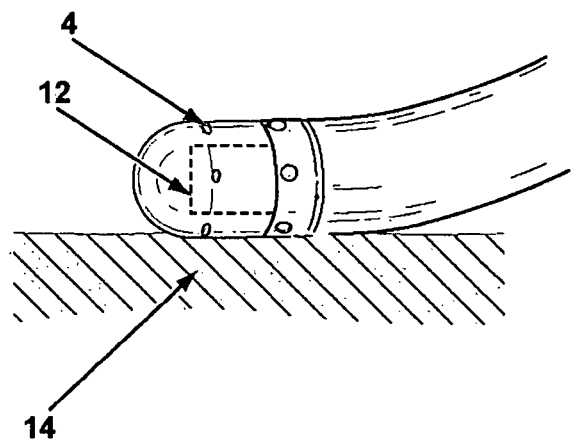
FIG. 4(a) shows an embodiment of an ablation catheter with the electrode assembly contacting the target tissue in a horizontal orientation.
Figure 4B:
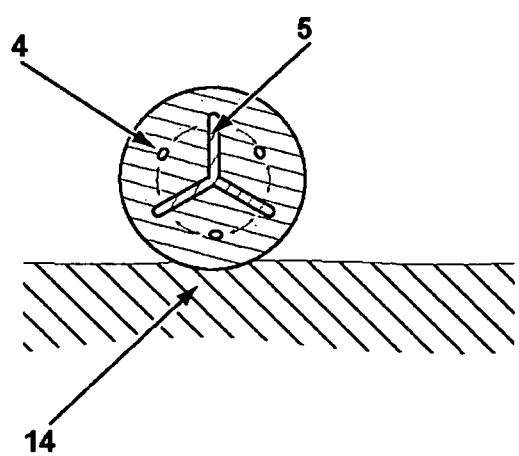
FIG. 4(b) shows a cross-sectional view of the ablation catheter of FIG. 4(a) illustrating the "Y" shape of the insulation member emanating from the center of the electrode body, and a symmetrical arrangement of three thermal sensors.

As described above, the placement of thermal sensors on a short catheter electrode necessarily means that the sensors would be located in closer proximity to one another than they would be on a longer electrode. Similarly, thermal sensors located around the circumference or a virtual circumferential line of an electrode having a relatively small diameter may also be quite close to one another. The excellent thermal conductivity of most electrode materials frequently means that the thermal energy producing high electrode temperatures on one section of the electrode is transmitted so quickly throughout the electrode that variations in temperature between sensors are negligible. As depicted in FIG. 4(b), the thermal energy can be transmitted to or among each of three thermal sensors (4) to essentially equalize the temperature at different points in the electrode even if the external surface at a certain point on the electrode actually has a higher temperature relative to other points. By separating the thermal sensors with a thermal insulating member (5), shown in FIG. 4(b) as a shaped member fitting into three radial slots bored into the electrode, the electrode is separated into multiple isothermal zones, each zone having one or more thermal sensors. Various thermal insulating member shapes, sizes, and material can be used. Preferably, the size, shape, and configuration of the thermal insulating member or members effectively separates at least two thermal sensors so more accurate temperature measurements from each sensor is possible over a period of time. Thus, one of the major advantages of the present invention is the use of insulating elements or members placed between temperature sensors within the electrode, which may function to thermally isolate thermal sensors and thus the precise location of elevated temperatures on the electrode external surface.

More specifically, FIG. 4(b) illustrates one placement of insulation member (5) between thermal sensors (4). The radial cross-sectional view of FIG. 4(b) shows three thermal sensors (4) distributed symmetrically around a circumferential line within the electrode. Also illustrated is the cross-sectional configuration of the insulation member or members (5). In the catheter orientation shown in FIG. 4(a), the portion of the electrode in contact with the tissue becomes warmer as the ablative energy from the electrode begins to raise the temperature of the tissue. This increase in electrode temperature will be detected by the thermal sensor (4) located closest to the tissue (14).

As noted earlier, in previous devices containing multiple sensors, the excellent thermal conductive properties found in most electrode materials would cause a very rapid transfer of the heat energy from the bottom temperature sensor toward the top sensors. Because of the short distance between sensors, the short, transient temperature differences between the temperature sensors would quickly be lost with previous devices.

FIG. 4(b) illustrates the advantages of adding an insulation member (5) between multiple temperature sensors (4) in the electrode. It will immediately be appreciated by those of skill in the art that the addition of an insulating member between the electrodes as shown will inhibit the rapid transfer of heat between temperature sensors and tend to create "zones" that conduct less thermal energy to other parts of the electrode. Thus, in FIG. 4(b), as the tissue temperature rises during the ablation, one would expect to see the reading of the bottom thermal sensor closest to the tissue (14) increase. However, with less opportunity to conduct heat toward the other thermal sensors, the remaining sensors would be expected to register cooler temperatures than sensor (4). The addition of insulating member or elements preserves the temperature differential between the thermal sensors. A variety of thermally insulative materials may be used to form the insulation member (5). Examples of thermally insulative materials include PEEK (polyetheretherketone), HDPE (high density polyethylene), Pebax (polyether block amides), nylon, polyurethane polymers and polyimides. Other thermal insulating materials known in the art or available can also be rendered into biocompatible sheets, strips, or layers to be adapted into the thermal insulating member or element as described in this invention.

FIG. 4(b) shows an insulating member with what is termed a "Y" shape, which creates symmetric isothermal zones around three symmetrically arranged thermal sensors. However, as described above, other numbers and arrangements of sensors are possible and/or desirable depending on the application. Insulating member materials and shapes may be created to suit any number of sensor combinations. For example, a symmetrical arrangements of four thermal sensors around the circumference of the electrode may make a "cross-shaped" insulation member a more appropriate choice of design. Alternatively, the use of five sensors may suggest use of a "star-shaped" insulation member. Insulation members can also be designed to accommodate asymmetric placement of sensors around the circumference. Any arrangement of insulating member which accomplishes the goal of creating isothermal zones within the electrode are expressly contemplated by this invention.

The utility of having an electrode able to accurately distinguish temperature differences around its circumference will be immediately appreciated by those skilled in the art. As an initial matter, the ability to measure and monitor the temperature at several points around an ablative element makes it much easier to gauge the maximum temperature being observed at a tissue site. This information provides the physician with an improved indication of how much power should be applied to an ablating electrode and how long it should remain in contact with the tissue. Additional accurate information regarding the maximum temperature being experienced at a tissue site also improves the safety of the patient during the procedure.

The ability to determine differentials in temperature across multiple sensors around the circumference of the electrode can provide other information to the physician as well. FIG. 5 illustrates an ablation catheter like the embodiment found in FIG. 4. FIG. 5 shows the catheter positioned in a variety of orientations or "contact angles" and with irrigation ports (11) in irrigation assembly (13) of catheter (2). In FIG. 5(c), the catheter is positioned in a manner as described above in FIG. 4 (the "side-firing" orientation or mode). The electrode is in full contact with the tissue along one side with one sensor (4) oriented in contact or very close proximity to the tissue (14), while the other sensors (4) are further removed. An increase in temperature associated with the bottom electrode would be expected during an ablation with this orientation with cooler temperatures associated with the other electrodes due to the thermal isolation provided by the insulating members between electrodes (not shown). Accordingly, a thermal profile showing increased temperature at one sensor (4) when compared to the remaining sensors would be an indication of the orientation of the catheter at that it was in "side-firing" mode.

Figure 5A:
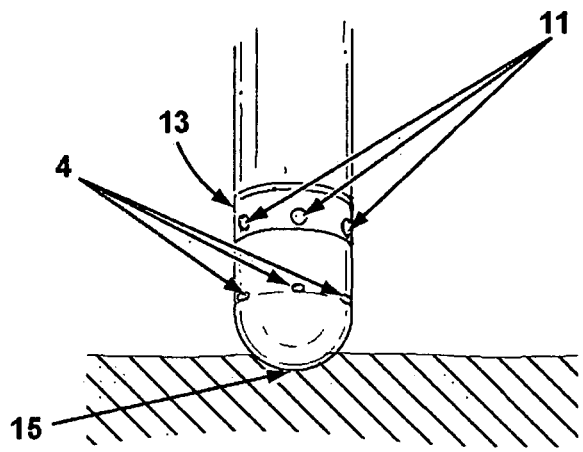
FIG. 5(a), (b), and (c) depict an embodiment of an ablation catheter electrode illustrating how the position of the thermal sensors differs depending on the contact angle and orientation of the electrode compared to the target tissue.

In contrast, the thermal sensor profile would look different in the orientation illustrated in FIG. 5(a). In this orientation, the "end-firing" mode, the temperature of the electrode would be expected to increase at the site of the tissue contact. Since no particular thermal sensor is closer than another in this orientation, the heat generated at the distal end "tip" of the electrode (15) would be conducted equally up through the electrode and that all three sensors would record a similar temperature measurement. Additionally, since the insulating members form isothermal zones in the electrode, it would be expected that heat would be conducted through each zone in substantially the same manner. Thus, an indication of elevated temperatures that were substantially equal across all of the thermal sensors would be an indication that the electrode was in "end-firing" mode.

In a situation where the electrode was not making contact with any tissue, one would expect that temperatures at all three sensor zones would also be substantially similar. However, since application of the electrodes energy in that situation would not be generating heat at a tissue site, one would expect the overall temperature level reading at the three sites to be lower than the orientation of FIG. 5(a) or that it would not change over a time period as it would in the end-firing mode of FIG. 5(a).

Figure 5B:
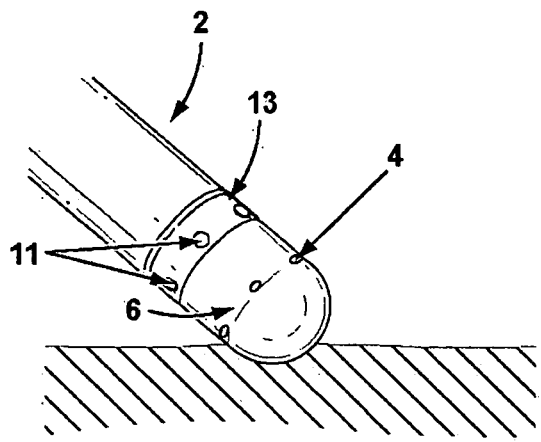
Figure 5C:
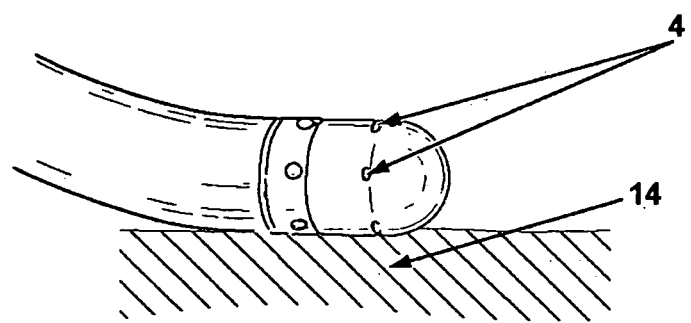

FIG. 5(b) illustrates an intermediate condition. Once again, heat energy will be generated at the site of tissue contact. Because the temperature sensor is not in direct contact with the tissue some of the heat energy may be dissipated in the blood or interstitial fluid and therefore the temperature would not reach as high a reading as in the FIG. 5(c) orientation. Nevertheless, in this orientation the insulation members running longitudinally up the catheter will tend to increase the temperature in one or more zones compared to other zones, although the increase is not as quick as in the situation of FIG. 5(c). It will be immediately appreciated that various contacting angles can be observed and the temperature differentials between sensors compared to produce a dataset that correlates the temperature differentials to various contact angles. Thus, the physician (or a computerized controller) could be provided with additional information helpful in determining the contact angle of the electrode with respect to the tissue. In response, the physician (or controller) would have the option of changing the contact angle or adjusting the power applied to the electrode in response to different treatment situations.

Figure 6:
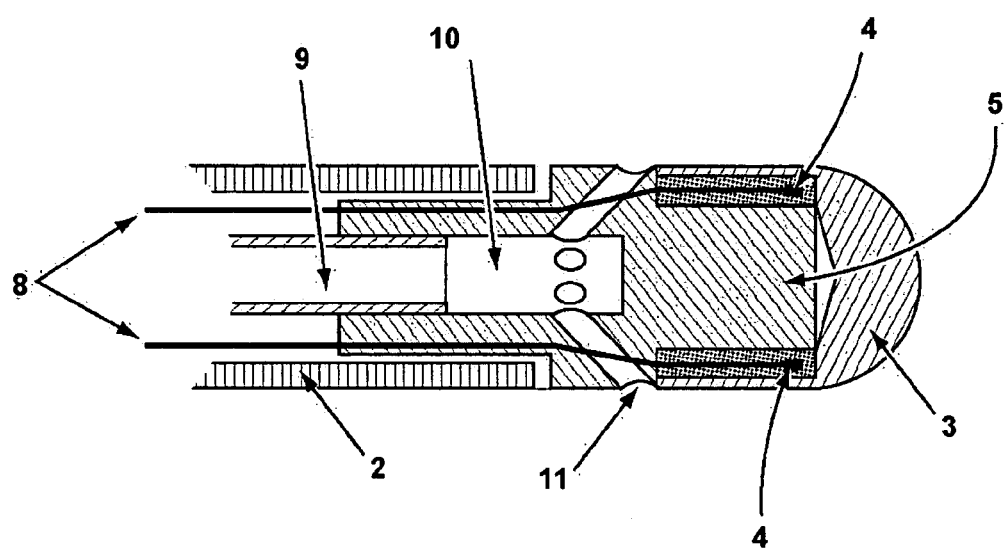
FIG. 6 shows an alternative embodiment of an ablation catheter including a tip electrode, thermal sensors located substantially the same distance from the distal end, insulation members between the thermal sensors, and an irrigation system that provides irrigated cooling fluid to the electrode and at or near the ablation site.

FIG. 6 illustrates an alternative embodiment of the ablation catheter which also incorporates an irrigation system for cooling of the electrode and/or surrounding tissue. An example of an irrigated cooling system of this type is found in application Ser. No. 11/434,220 filed on May 16, 2006, the entire contents of which are incorporated herein by reference. This embodiment incorporates the additional elements of a fluid tube (9) through the shaft (2) of the catheter, which provides cooling irrigation fluid to the electrode (3) through ports (11). A manifold (10) connects a fluid flow tube (9) or passageway to fluid ports (11) that exit the catheter in close proximity to the electrode. The addition of an irrigation system provides the physician with an additional method of controlling ablation temperature in response to the information provided by the multiple thermal sensors (4). In FIG. 6, the thermal sensors (4) are positioned at substantially the same distance from the end of the electrode (3) and within slots or holes cut near the external surface of the electrode. The region for thermal insulation member (5) can be a single, large hollowed region filled with one or more insulting members or elements and then sealed or filled with an appropriate polymer or adhesive. The adhesive can also fix the position of the electrode (3) on the distal end of catheter (2) with the irrigation manifold (10). Just as space considerations may affect the number of thermal sensors that can be incorporated in an electrode, addition of an irrigation system may impose restrictions on thermal sensor placement and number. However, the placement and operation of thermal sensors and insulation members in the electrode would be no different in principle in a catheter incorporating an irrigation system than it would be in embodiments already described.

Although several embodiments of this invention have been described above with a certain degree of particularity, those skilled in the art could make numerous alterations to the disclosed embodiments without departing from the spirit or scope of this invention. For example, although placement of thermal sensors has been described primarily in terms of circumference line around the electrode, numerous other arrangements of thermal sensors could be adapted without departing from the scope of this invention. Similarly, a wide variety of insulating materials and techniques are possible.

An important feature of this invention is providing accurate temperature information about the treatment tissue to the physician. Many different techniques for displaying and processing temperature information are conceived. The sensor leads may be attached to monitoring equipment which provides the physician with temperature information in the form a visual display. In alternative embodiments, feedback from the thermal sensors could also be routed to a computer or controller which monitors and compares temperature information to certain pre-set thresholds and controls the application of ablation energy accordingly.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrode for an ablation catheter, comprising:
   an electrode having a distal tip, a partially hollowed core region, and a proximal region;
   at least two thermal sensors to an interior portion of the partially hollowed core region of the electrode; and
   at least one thermal insulation member positioned to thermally shield each one of the at least two thermal sensors from each other of the at least two thermal sensors,
   wherein the electrode length equals at least one of the electrode diameter and the electrode cross-sectional length, and
   wherein each thermal sensor is fixed at the same distance from the distal tip within the interior portion of the hollowed core region of the electrode.

2. The electrode of claim 1, wherein the catheter comprises an irrigated ablation catheter.

3. The electrode of claim 1, wherein the electrode has a cylindrical proximal region and a distal dome-shaped tip and is about 2.5 mm or less in length.

4. The electrode of claim 1, wherein the thermal sensors are thermocouple sensors.

5. The electrode of claim 1, wherein the at least two thermal sensors are thermistor sensors.

6. The electrode of claim 1, wherein the at least two thermal sensors are a combination of thermocouple and thermistor sensors.

7. The electrode of claim 1, wherein the at least two thermal sensors are symmetrically distributed within the hollow core region.

8. The electrode of claim 1, wherein three or more thermal sensors are symmetrically distributed within the hollowed core region.

9. The electrode of claim 8, wherein at least three thermal insulation members separate the three or more thermal sensors.

10. The electrode of claim 1, wherein four or more thermal sensors are symmetrically distributed within the hollowed core region.

11. The electrode of claim 10, wherein four thermal insulation members separate four thermal sensors.

12. The electrode of claim 1, wherein the electrode is made of Pt or a Pt/Ir alloy.

13. The electrode of claim 1, wherein at least one thermal sensor is positioned within the hollowed core region approximately 0.25 mm or less from the external surface of the electrode.

14. The electrode of claim 1, wherein the thermal insulation member comprises one or more polymer compositions.

15. The electrode of claim 14, wherein the one or more polymer compositions is selected from PEEK (polyetheretherketone), HDPE (high density polyethylene), Pebax (polyether block amides), nylon, polyimides, or polyurethane polymers.

* * * * *